PRIOR ART

United States Patent [19]

Siri

[11] Patent Number: Plant 5,731

[45] Date of Patent: Apr. 29, 1986

[54] MINIATURE CARNATION—BALLERINA

[75] Inventor: Angelo J. Siri, San Francisco, Calif.

[73] Assignee: Sir Brothers Nursery, Inc., East Palo Alto, Calif.

[21] Appl. No.: 641,918

[22] Filed: Aug. 17, 1984

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A carnation plant having petals which are a soft white with bright pink edging.

2 Drawing Figures

BACKGROUND OF THE NEW PLANT

This invention comprises a new and distinct miniature carnation variety that has its own set of characteristics that set it apart from all other varieties of miniature carnations. The newly discovered variety, called "Ballerina," originated as a sport of Aquarius, an unpatented variety.

The botantical classification of the new variety is *Dianthus caryophyllus longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif., by taking cuttings. The cuttings so taken and grown have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
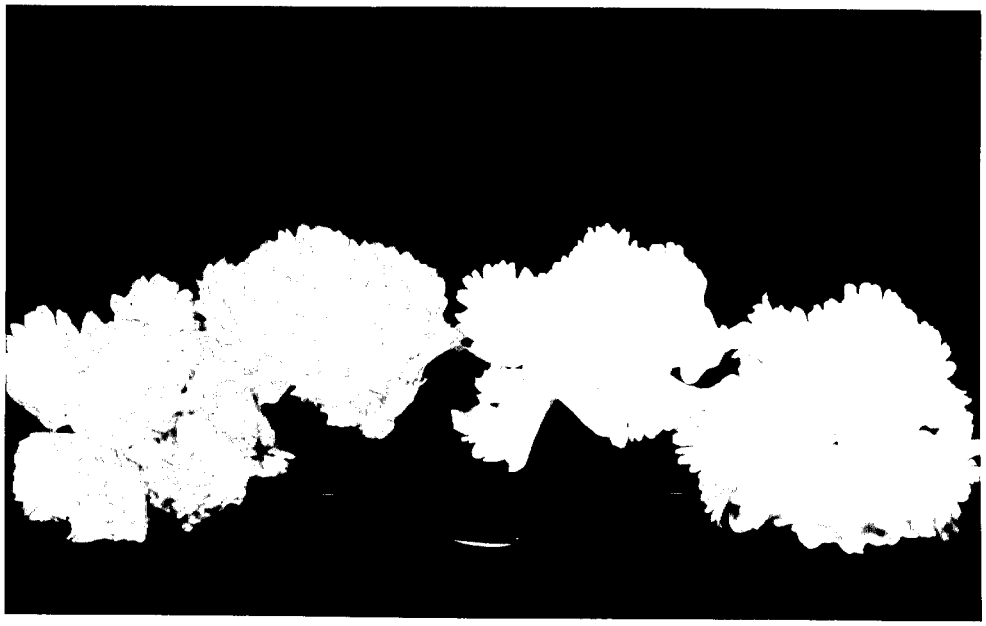
FIG. 1. PRIOR ART
FIG. 1 is an enlarged view of the bloom of the new variety Ballerina on the right and showing the parent Aquarius on the left.
Figure 2:
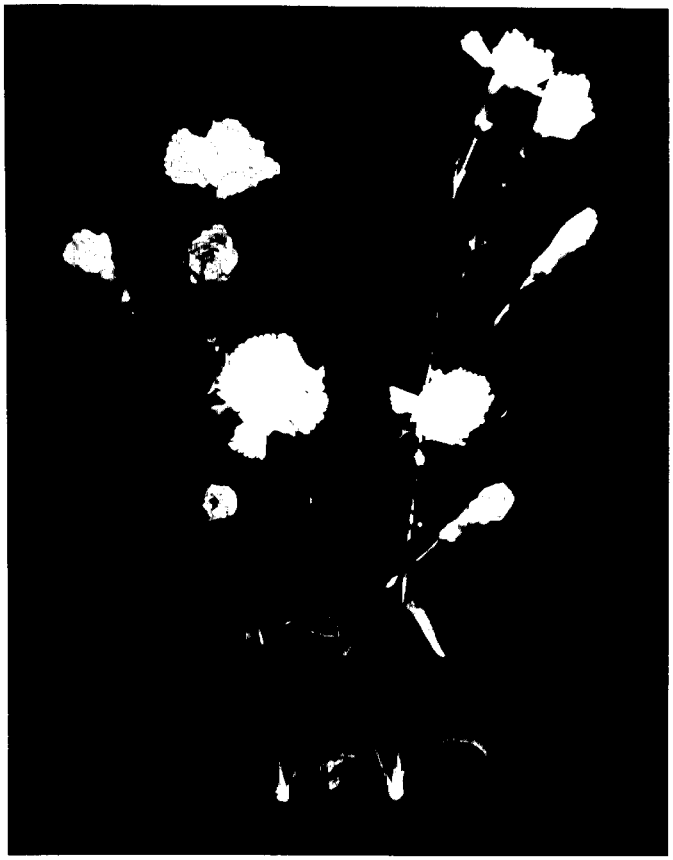
FIG. 2 is a view of the sprays of the new variety Ballerina on the right and the prior art Aquarius on the left.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "R.H.S." for Royal Horticultural Colour Chart, The Royal Horticultural Society, London, England.

GROWTH HABITS

Height: Average.

Foliage: Average.

Speed of growth: Slightly below average but faster than it's parent.

Root system: Average.

FOLIAGE

Leaf size:

*Length.*—Averages $4\frac{3}{4}''$ at midstem.

*Width.*—Averages $\frac{3}{8}''$ at midstem.

*Features.*—N/A.

Leaf shape: Average curl with a long accuminating tip.

Leaf texture: Smooth and leathery.

Leaf color:

*Upperside.*—R.H.S. Green Group 139A with a whitish color over the green.

*Underside.*—R.H.S. Green Group 139A with a whitish color over the green.

Leaf ribs: One rib down the center from the base to the tip of the leaf.

Leaf habit: Average amount of curl.

Leaf density: Slightly less than average.

STEM

Stem strength: Above average extremely strong.

Stem color: R.H.S. Green Group 139A with a whitish color over the green.

Nodes: Large.

*Space between nodes.*—$2\frac{1}{2}$ at midstem.

Stem branching: Above average, not clubby, wide separations.

BUDS

Bud shape: Oval.

Bud color: The top half is LCC H-22 L-12, the bottom half blends into LCC H-22 L-19.

Average number of flowering buds per stem: 5 to 6.

Uniformity of bud opening: Very uniform.

Bud splitting: Very seldom.

Number of sepals per calyx: 85% of calyxs have 5.15% of calyxs have 6.

FLOWER

Description of the color of the bloom: The bloom is white, R.H.S. White Group 155D with Pink edging, LCC H-42 L-6.

General tonality of the color: Soft due to the white but bright due to the pink edging.

Diameter of average bloom: $2\frac{1}{2}$ inches.

Bloom shape: Generally round with a high center and flat outer petals.

Keeping quality: Average.
Fragrance: Very noticeable.

PETALAGE

Petal texture: Soft and smooth.
Petal edge: Very serated.
Color stability: Extremely stable.
Petal size:
*Average length.*—2".
*Average width at widest point.*—1¼".
Calyx color: The top half is LCC H-22 L-12, the bottom blends into LCC H-22 L-9, the tips of the leaves at the bottom of the calyx are LCC H-19 L-15.

REPRODUCTIVE ORGANS

Stamen: With anthers.
Average length of stamen: They average 1 1/16 ".
Color of anthers: LCC H-26 L-1.
Color of filament: Light green LCC H-24 L-1.
Pistils:
*Shape.*—Almost all the pistils have 2 styles.
*Number.*—1.
*Length from tip to ovary.*—1½" average.
Stigma:
*Shape.*—Round.
*Color.*—White.
Style:
*Color.*—Slightly off white.
Ovary:

*Shape.*—Ovid.
*Color.*—The tip is LCC H-26 L-11, the middle is LCC H-22 L-11, the bottom is LCC H-23 L-2.
*Length.*—It averages 5/16".
*Width.*—It averages ¼".

DISTINGUISHING CHARACTERISTICS BETWEEN THE NEW VARIETY AND PARENT

There are several distinguishing characteristics. The new variety is a completely different color than the parent. The parent has a pale yellowish background with deep purple edging, while the new variety has a white background with pink edging. The new variety grows faster than the parent. It will ome to flower approximately three weeks sooner than the parent. The fragrance of the new variety is slightly more noticeable than that of the parent.

SIMILAR CHARACTERISTICS OF THE NEW VARIETY AND PARENT

All the characteristics of both varieties are similar except for the distinguishing characteristics referred to above.

Years of asexual reproduction: 1982, 1983, 1984.

I claim:

1. A new and distinct variety of miniature carnation plant, substantially as herein shown and described.

* * * * *